United States Patent [19]

Miyake et al.

[11] Patent Number: 4,901,024
[45] Date of Patent: Feb. 13, 1990

[54] APPARATUS FOR ANALYZING AND SEPARATING PARTICLES AND A SYSTEM USING THE SAME

[75] Inventors: Shinichi Miyake; Masayuki Kometani, both of Osaka, Japan

[73] Assignee: Sumitomo Electric Industries Ltd., Osaka, Japan

[21] Appl. No.: 124,596

[22] Filed: Nov. 24, 1987

[30] Foreign Application Priority Data

Jan. 20, 1987 [JP] Japan .................................. 62-8887

[51] Int. Cl.[4] ........................................... G01N 27/00
[52] U.S. Cl. .................... 324/438; 324/71.4; 324/71.1
[58] Field of Search ............... 324/71.4, 71.1, 438, 324/439, 466

[56] References Cited

U.S. PATENT DOCUMENTS

| | | | |
|---|---|---|---|
| 3,979,669 | 9/1976 | Godin | 324/71.1 |
| 4,180,091 | 12/1979 | Hanley et al. | 324/71.4 |
| 4,434,398 | 2/1984 | Berg | 324/71.4 |
| 4,484,134 | 11/1984 | Halloran | 324/71.1 |
| 4,609,876 | 2/1986 | Reich | 324/438 |

Primary Examiner—Reinhard J. Eisenzopf
Assistant Examiner—Maura K. Regan
Attorney, Agent, or Firm—Cushman, Darby & Cushman

[57] ABSTRACT

A particle analyzer which comprises a constricted passage for the passage of fine particles contained in a suspension therethrough for isolation, upstream and downstream passages communicated with the constricted passage and positioned on upstream and downstream sides of the constricted passage with respect to the direction of flow of the suspension, a detector including upstream and downstream electrodes disposed in the upstream and downstream passages, respectively, so as to confront with each other for detecting the fine particles being passed through the constricted passage, and a cleansing passage communicated with either one of the upstream and downstream passages for the supply of a cleansing liquid.

6 Claims, 7 Drawing Sheets

APPARATUS FOR ANALYZING AND SEPARATING PARTICLES AND A SYSTEM USING THE SAME

BACKGROUND OF THE INVENTION

1. Field of the Invention

The present invention generally relates to a particle analysis and, more particularly, to a particle analyzer for individually separating and then injecting fine particles contained in a suspension or solution. The present invention also relates to a system utilizing the particle analyzer.

2. Description of the Prior Art

As a device designed to individually separate fine particles contained in a suspension and for counting the number of the fine particles, a particle analyzer of a construction shown in FIG. 10 of the accompanying drawings has long been well known in the art.

Referring to FIG. 10 for the discussion of the prior art, the particle analyzer 13 shown therein comprises a constricted passage 1 for the passage of the individual fine particles 6 and having upstream and downstream passages 2 and 3 communicated with the constricted passage 1 and positioned on respective sides of the constricted passage 1 with respect to the direction of flow of the suspension. The particle analyzer 13 also comprises upstream and downstream electrodes 4 and 5 disposed inside the upstream and downstream passages 2 and 3, respectively.

In this construction, when the suspension 30 containing the fine particles 6 is allowed to flow in a direction shown by the arrow A, the fine particles 6 can be individually separated and, therefore, change in impedance between the upstream and downstream electrodes 4 and 5 can be detected. If the frequencY of change in impedance is subsequently counted, the number of the fine particles 6 can be counted.

In other words, according to the prior art, a voltage is monitored when a predetermined electric current is supplied across the electrodes 4 and 5, but an electric current is monitored when a predetermined voltage is applied to the electrodes 4 and 5. Since the impedance across the electrodes 4 and 5 depends on internal conditions of the constricted passage 1 and external conditions in the vicinity of the constricted passage 1, the impedance undergoes change each time the fine particles pass through the constricted passage, which change can be detected in the form of pulses, the number of pulses representing the number of the fine particles having passed through the constricted passage 1.

After the number of the fine particles has been detected in the manner as hereinabove described with tee use of the particle analyzer 13, and when the fine particles contained in the detected suspension are to be injected into suitable containers, the containers are to be arranged immediately beneath the downstream passage 3. While the containers are conveyed successively past a position immediately beneath the downstream passage 3, a predetermined number of the fine particles is injected into each container.

However, the prior art particle analyzer and the prior art system utilizing such particle analyzer have been found having the following problems, particularly when the fine particles are continuously separated and injected with the use of the prior art particle analyzer.

(a) Some of the fine particles separated and injected during the previous cycle tend to be left within the flow system including the constricted passage and the upstream and downstream passages. The fine particles so left within the flow system will be flushed out with the fine particles allowed to flow during the subsequent cycle and, therefore, the fine particles different in number from the required number tends to be injected.

(b) Where the concentration of the fine particles in the suspension is high, the individual separation of the fine particles is difficult to achieve because the fine particles continuously pass through the constricted passage, and, therefore, the number of pulses generated will not accurately coincide with the number of the fine particles counted.

This problem may be substantially alleviated if the suspension is diluted before the detection and counting are performed, however, the time required to perform the detection and the counting will be prolonged and a time-consuming and complicated handling procedures will be required.

(c) Since a predetermined electric current is applied to the electrodes 4 and 5 within the upstream and downstream passages 3 and 4, hydrolysis tends to occur accompanied by the production of hydrogen gas which subsequently forms bubbles. As the bubbles of hydrogen gas pass through the constricted passage 1, and if the bubbles are of a size comparable to the size of the fine particles, the bubbles will be erroneously taken as the fine particles, resulting in a detection error.

SUMMARY OF THE INVENTION

Accordingly, the present invention has been devised with a view to substantially eliminate the above discussed problems inherent in the prior art particle analyzer and the prior art system utilizing the existing particle analyzer and has for its essential object to provide an improved particle analyzer capable of accurately separating and injecting fine particles in the suspension even when the fine particles are continuously supplied so as to flow through the particle analyzer.

Another important object of the present invention is to provide an improved particle analyzing system utilizing the improved particle analyzer of the type referred to above.

According to the present invention, there is provided a particle analyzer which comprises a constricted passage means for the passage of fine particles contained in a suspension therethrough for isolation; upstream and downstream passage means communicated with the constricted passage means and positioned on upstream and downstream sides of the constricted passage means with respect to the direction of flow of the suspension; a detecting means including upstream and downstream electrodes disposed in the upstream and downstream passage means, respectively, so as to confront with each other for detecting the fine particles being passed through the constricted passage means; and a cleansing passage means communicated with either one of the upstream and downstream passage means for the supply of a cleansing liquid.

According to the present invention, there is also provided a particle analyzing system which comprises the particle analyzer; a container for accommodating the suspension and communicated with the upstream passage, said suspension being supplied to the particle analyzer by means of a valving operation; a discharge piping leading from the downstream passage means to a discharge port and having a valve disposed thereon for controlling the discharge of the suspension which has flowed through the constricted passage means; a cleansing liquid supply piping extending from a source of the cleansing liquid to the cleansing passage means and having a valve disposed thereon for controlling the supply of the cleansing liquid; and a sensor included in the detecting means for detecting the change in impedance between the upstream and downstream electrodes.

In the practice of the present invention, the particle analyzer may have a diluting liquid passage means communicated with the upstream passage means for supplying a diluting liquid for the dilution of the suspension.

With this construction according to the present invention, even when the concentration of the fine particle in the suspension or solution is high, the fine particles can be accurately, easily and quickly separated and injected. Also, the detection of the fine particles can be accomplished without being disturbed by bubbles of hydrogen gas which is generated as a result of hydrolysis of water.

DESCRIPTION OF THE EMBODIMENTS

Figure 1A:
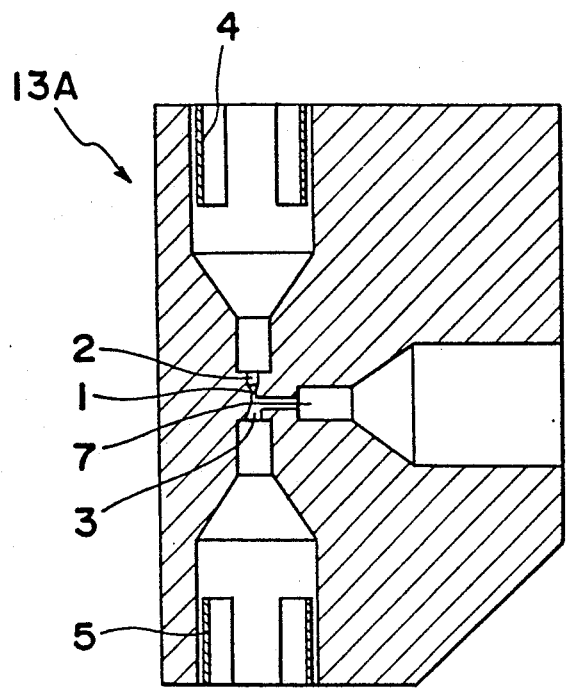
FIG. 1(a) is a schematic longitudinal sectional view of a particle analyzer according to one embodiment of the present invention.

Before the description of the present invention proceeds, it is to be noted that like parts are designated by like reference numerals throughout the accompanying drawings.

(Embodiment I)

Figure 1B:
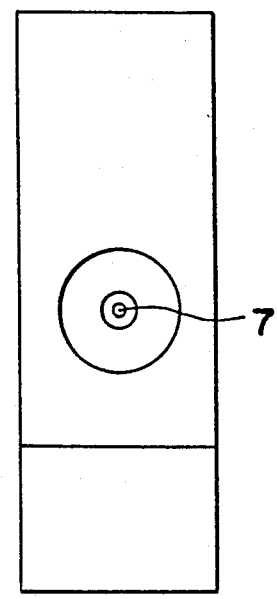
FIG. 1(b) is a bottom plan view of the particle analyzer of FIGS 1(a)
Figure 1C:
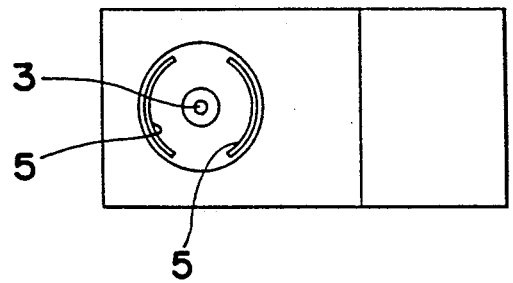
FIG. 1(c) is a top plan view of the particle analyzer of FIG. 1(a)

Referring to FIGS. 1(a) to 1(c) illustrating a first preferred embodiment of the present invention, a particle analyzer disclosed therein and generally identified by 13A is so designed and so constructed as to isolate or separate particles in suspension and also to count the number of the particles for the subsequent fraction of the particles. The illustrated particle analyzer 13A comprises a solid block having defined therein a generally elongated constricted passage 1 for the passage of fine particles in suspension therethrough for isolation, said constricted passage 1 having its opposite end communicated respectively with upstream and downstream passages 2 and 3, and a cleansing passage 7 having one end communicated to a source of cleansing liquid and the other communicated with the downstream passage 3 adjacent the constricted passage 2. Each of the downstream passage 3 and the cleansing passage 7 has a diameter at least twice the diameter of the constricted passage 2 such that the suspension containing the fine particles can be passed efficiently. If the diameter of each of the downstream passage 3 and the cleansing passage 7 is smaller than twice the diameter of the constricted passage 2, a relatively large resistance will act on the flow of the suspension.

The constricted passage 2 is so sized as to have a diameter within the range of 2 to 20 times the particle size of the fine particles to be analyzed. Should the diameter of the constricted passage 2 be smaller than the lower limit, the fine particles be passed efficiently without difficulties and no change in impedance required for the detection will be observed.

(Embodiment II)

Figure 2:
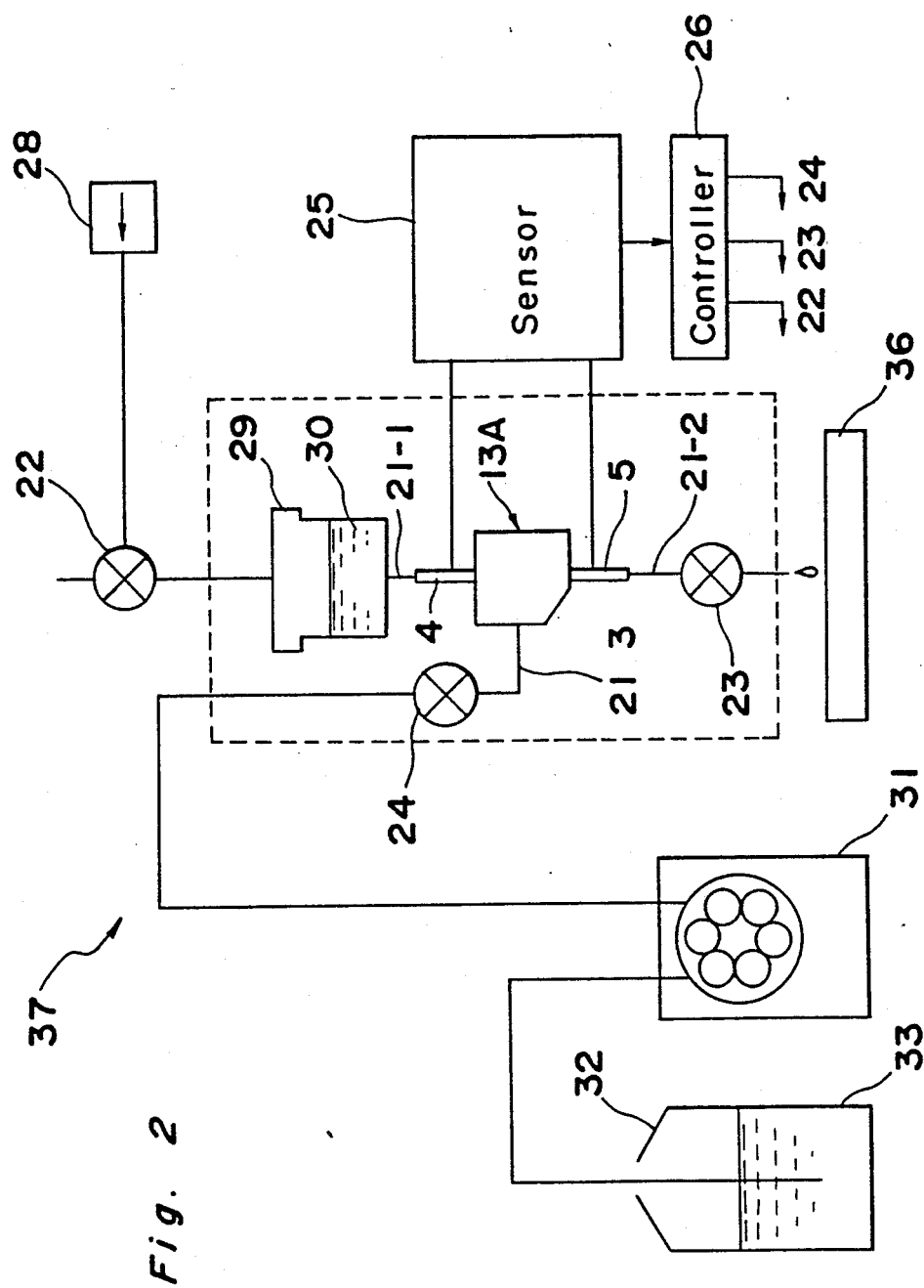
FIG. 2 is a diagram showing a particle analyzing system utilizing the particle analyzer of FIG. 1.

Referring to FIG. 2, there is shown a particle analyzing system utilizing the particle analyzer 13A of the construction shown in and described with reference to FIGS. 1(a) to 1(c). The particle analyzing system is generally identified by 37 includes a supply piping 21-1 connecting the upstream passage 2 of the particle analyzer 13A to a tank 29 filled with a quantity of the suspension 30 containing the particles 6 to be analyzed and fractioned. The tank 29 is of a type substantially sealed after the quantity of the suspension 30 has been charged, such that, when an electromagnetic valve 22 disposed on a line extending between the tank 29 and a pump 28 is opened, a gaseous medium pressurized by the pump 28 can be supplied via the electromagnetic valve 22 into the tank 29 to urge the solution 30 to flow towards the particle analyzer 13A through the supply piping 21-1. The solution so urged subsequently flows through the constricted passage 1 through the upstream passage 2 in the particle analyzer 13A.

The particle analyzer 13A has, as shown in FIGS. 1(a) and 1(b), upstream and downstream electrodes 4 and 5 which are electrically connected with an impedance sensor 25 so designed and so operable as to detect the fine particles in terms of the amount of change in impedance which occurs as a result of the passage of the fine particles through the constricted passage 1.

The downstream passage 3 is fluid-coupled with an electromagnetic valve 23 which is in turn fluid-coupled with a discharge line disposed immediately above a collecting vessel 36. The electromagnetic valve 23 is so operable as to allow a controlled quantity of the suspension, which has flowed through the constricted passage 1, to be injected into the collecting vessel 36 through the discharge line when it is opened, but as to retain the suspension within the system between the electromagnetic valve 23 and the tank 29 when and so long as it is closed.

The cleansing passage 7 shown in and described with reference to FIGS. 1(a) to 1(c) is communicated with a source of cleansing liquid through a liquid piping 21-3 having an electromagnetic valve 24 and a rotary pump 31 both disposed on such liquid piping 21-3. The source of cleansing liquid is, in the instance as shown, constituted by a liquid vessel 32 containing a quantity of cleansing liquid 33. The electromagnetic valve 24 when opened while the rotary pump 31 is in operation allows the cleansing liquid to be supplied into the cleansing passage 7.

The electromagnetic valves 22, 23 and 24 used in the system of FIG. 2 are controlled in a predetermined sequence by commands issued from a controller 26 which is operated in response to an output signal generated from the sensor 25.

When the particles in the suspension are desired to be detected with the particle analyzing system 37, the electromagnetic valve 22 is opened and, the pump 28 is operated to apply a gas pressure to the suspension 30 within the tank 29. The application of the gas pressure thus causes the suspension 30 to flow towards the particle analyzer 13A through the supply piping 21-1 and then towards the collecting vessel 36 through the discharge piping 21-2 after having passed through the constricted passage 1 in the particle analyzer 13A. At this time, the electromagnetic valve 23 is also opened to allow the suspension which has flowed through the constricted passage 1 to flow therethrough towards the collecting vessel 36. The electromagnetic valve 24 is, however, closed during the flow of the suspension through the particle analyzer 13A.

As the particles contained in the suspension pass through the constricted passage 1, the sensor 25 detects the change in impedance and generates a detection output signal which is in turn applied to the controller 26. In response to the output signal from the sensor 25, the controller 26 issues disabling commands to the electromagnetic valves 22 and 23, respectively. The electromagnetic valves 22 and 23 are closed in response to the respective disabling commands from the controller 26, thereby interrupting the supply of the suspension 30 through the particle analyzer 13A. When the electromagnetic valves 23 and 24 are subsequently opened while the electromagnetic valve 22 remains closed, the operation of the rotary pump 31 causes the cleansing liquid 33 to be supplied from the liquid vessel 32 towards the particle analyzer 13A through the electromagnetic valve 24 by way of the liquid piping 21-3 and, then, through the cleansing passage 7 into the downstream passage 3 while purging into the collecting vessel 36 the fine particles which have passed through the constricted passage 1. Where the fine particles are desired to be individually collected each in one vessel, a row of vessels 36 should be conveyed to a position immediately below the discharge piping 21-2 and, for this purpose, a conveyor carrying the vessels 36 may be controlled in dependence on the output signal generated from the sensor 25.

In the embodiment shown in FIG. 2, the supply of the suspension 30 and the cleansing liquid 33 to the upstream passage 2 in the particle analyzer 13A has been shown and described as controlled by the use of the separate electromagnetic valves 22 and 24. However, a variant of the particle analyzing system shown by 37A in FIG. 4, a single electromagnetic valve is employed for controlling the supply of the suspension 30 and the cleansing liquid 33.

Figure 3A:
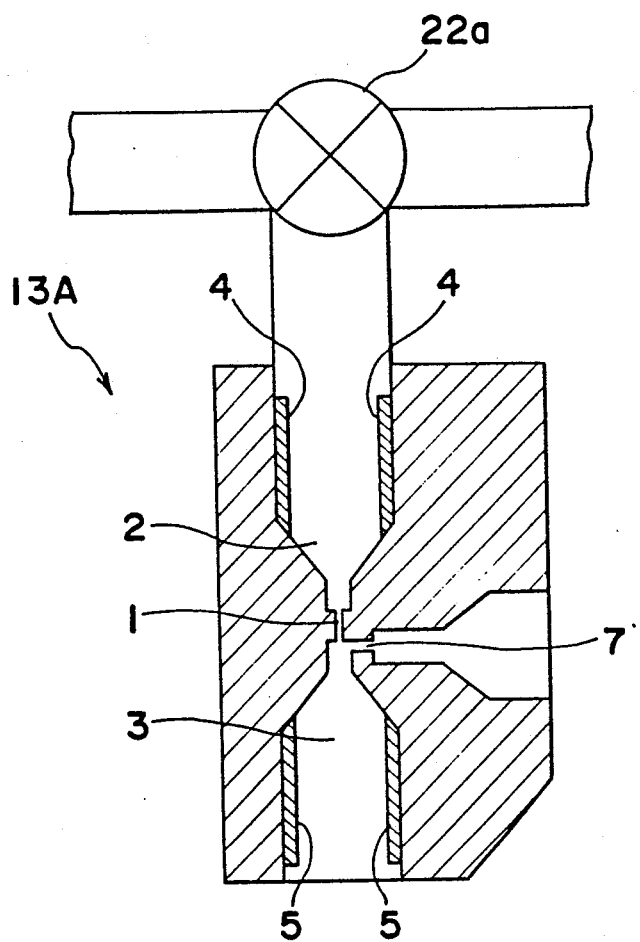
FIG. 3(a) is a schematic longitudinal sectional view showing a modified form of the particle analyzer of FIG. 1.
Figure 3B:
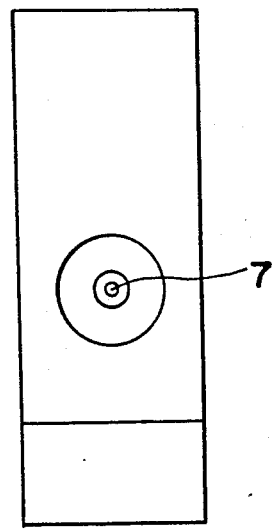
FIG. 3(b) is a bottom plan view showing a modified form of the particle analyzer of FIG. 1.
Figure 3C:
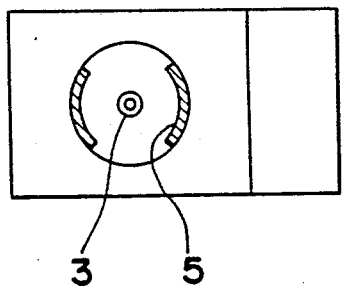
FIG. 3(c) is a top plan view showing a modified form of the particle analyzer of FIG. 1.
Figure 4:
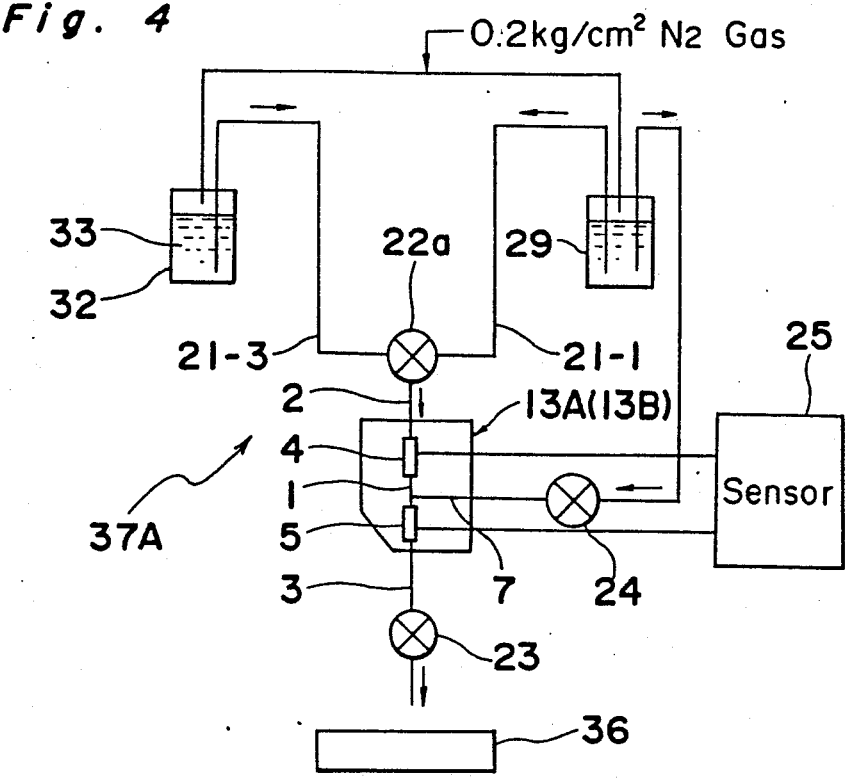
FIG. 4 is a diagram generally similar to FIG. 2, showing the particle analyzing system utilizing the particle analyzer of FIG. 3.

Referring now to FIGS. 3 and 4, the single electromagnetic valve referred to above is identified by 22a and is in the form of a three-way electromagnetic valve having three ports which are fluid-connected with the supply piping 21-1, the liquid piping 21-3 and the upstream passage 2, respectively. The electromagnetic valve 22a has first and second operative positions; said electromagnetic valve 22a is in position to communicate the supply piping 21-1 with the upstream passage 2, when in the first operative position, and in position to communicate the liquid piping 21-3 with the upstream passage 2 when in the second operative position. Instead of the use of the separate pumps 28 and 31, the tank 29 and the vessel 32 are so designed as to be simultaneously pressurized by the supply of a pressurized $N_2$ gas from a common source of $N_2$ gas (not shown). Thus, it will readily be understood that, depending on the operative position of the electromagnetic valve 22a, either the suspension in the tank 29 or the cleansing liquid in the vessel 32 can be supplied to the particle analyzer through the electromagnetic valve 22a.

It is to be noted that, in the foregoing description of each of the first and second embodiments made with reference to FIG. 1 to FIG. 3, the cleansing passage 7 has been described and shown as communicated with the upstream passage 2, it may be communicated with the downstream passage 3. It has, however, been found that, if the cleansing passage 7 is communicated with either the upstream passage 2 or the downstream passage 3 at a location upstream of the associated electrode 4 or 5 with respect to the direction of flow of the suspension, the cleansing efficiency can be increased.

(Embodiment III)

Figure 5:
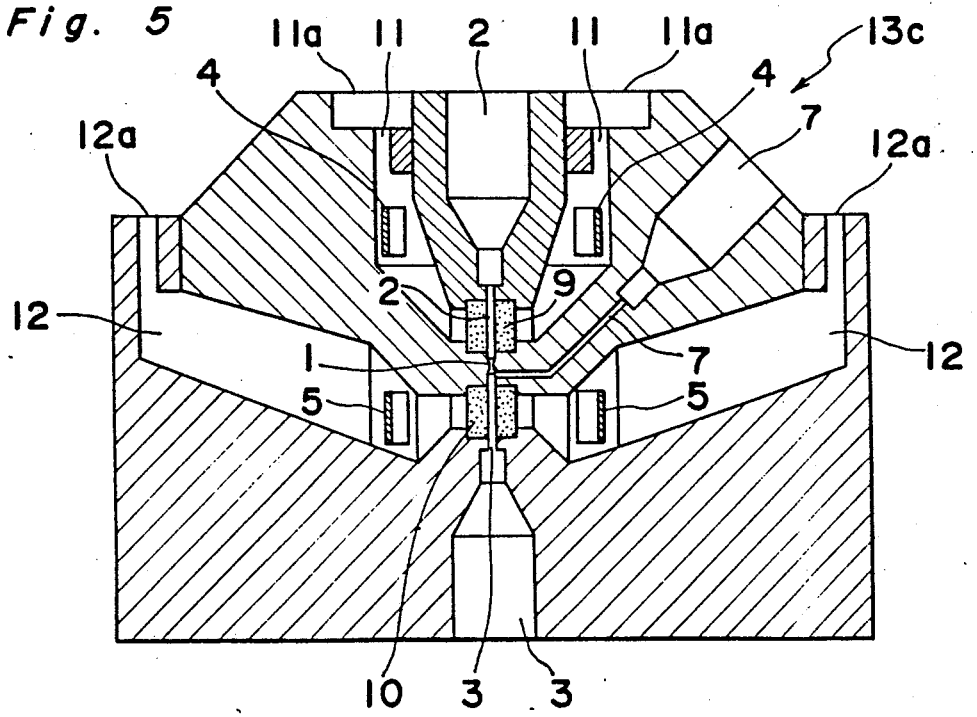
FIG. 5 is a longitudinal sectional view of the particle analyzer according to another embodiment of the present invention.

A third preferred embodiment of the particle analyzer according to the present invention is shown in FIG. 5 and generally identified by 13C.

The particle analyzer 13C comprises a solid block having defined therein a generally elongated constricted passage 1 for the passage of fine particles in suspension therethrough for separation, said constricted passage 1 having its opposite end communicated respectively with upstream and downstream passages 2 and 3, and a cleansing passage 7 having one end communicated to a source of cleansing liquid and the other communicated with the downstream passage 3 adjacent the constricted passage 2. The solid block also has an upstream reservoir 11 and a downstream reservoir 12 defined therein and positioned exteriorly of the upstream and downstream passages 2 and 3, respectively. The upstream reservoir 11 and the upstream passage 2 are partitioned by a porous glass 9 having fine pores of a size effective to pass ions therethrough, but to block vapor bubbles comparable in size to the fine particles to be passed through the constricted passage 1, so that the suspension can freely flow between the upstream reservoir 11 and the upstream passage 2. Similarly, the downstream reservoir 12 and the downstream passage 3 are partitioned by a porous glass 9 having fine pores of a size effective to pass ions therethrough, but to block vapor bubbles comparable in size to the fine particles to be passed through the constricted passage 1, so that the suspension can freely flow between the downstream reservoir 12 and the downstream passage 3. The upstream and downstream electrodes 4 and 5 are accommodated within the upper and lower reservoirs 11 and 12, respectively, so as to confront with each other.

The upstream reservoir 11 is opened at 11a to the outside for the discharge of hydrogen gas bubbles which will be produced as a result of hydrolysis which takes place when an electric current is supplied across the upstream electrodes 4 while the suspension remains within the upstream passage 2. Similarly, the downstream reservoir 12 is opened at 12a to the outside for the discharge of hydrogen gas bubbles which will be produced as a result of hydrolysis which takes place when an electric current is supplied across the downstream electrodes 4 while the suspension remains within the downstream passage 3.

As hereinbefore described in connection with the foregoing embodiments, the upstream and downstream electrodes 4 and 5 are connected with the sensor 25 for the detection of the fine particles contained in the suspension and being isolated during the flow thereof through the constricted passage 1.

Where the particle analyzing system is assembled by the use of the particle analyzer 13C of the construction shown in and described with reference to FIG. 5, either the fluid circuit shown in FIG. 2 or the fluid circuit shown in FIG. 4 may be employed.

The particle analyzer of the construction shown in and described with reference to FIG. 5 makes use of members, such as the porous glasses, having micropores which, when bubbles are produced as a result of generation of hydrogen gas incident to the hydrolysis of water which takes place when the electric current is supplied across the electrodes, permit the passage of ions, but block the passage of the bubbles. Therefore, any possible error in detection which would result from disturbance by the bubbles can be effectively avoided to accomplish an accurate separation of the fine particles contained in the suspension.

In addition, as is the case with any one of the foregoing embodiments, the supply of the cleansing liquid through the cleansing passage 7 makes it possible to purge the particles remaining inside the passage in the particle analyzer, which feature compounds to the capability of more accurate separation of the fine particles in the suspension.

(Embodiment IV)

Figure 6A:
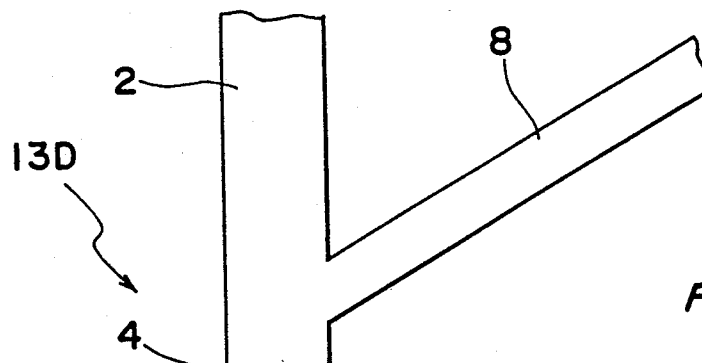
FIG. 6(a) is a schematic longitudinal sectional view showing the particle analyzer according to a further embodiment of the present invention.
Figure 6B:
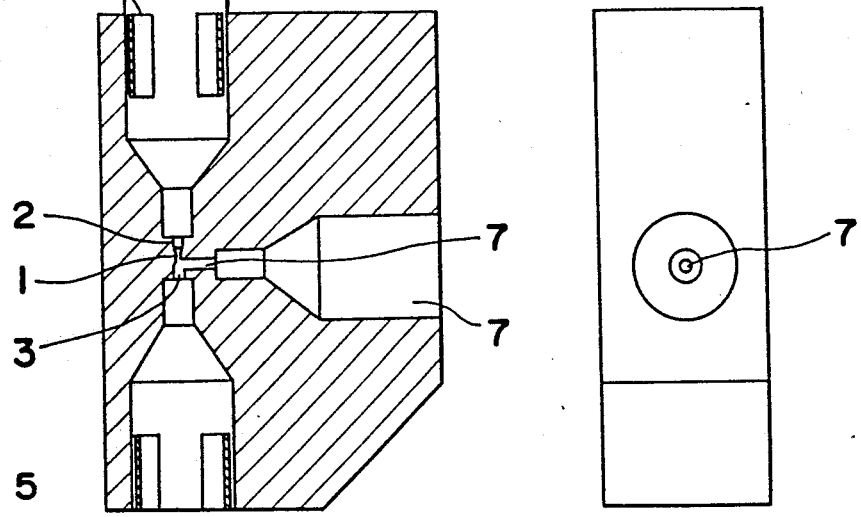
FIG. 6(b) is a bottom plan view showing the particle analyzer according to a further embodiment of the present invention.
Figure 6C:
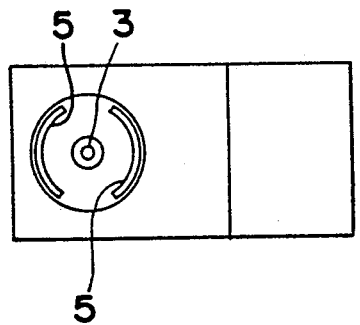
FIG. 6(c) is a top plan view showing the particle analyzer according to a further embodiment of the present invention.
Figure 7:
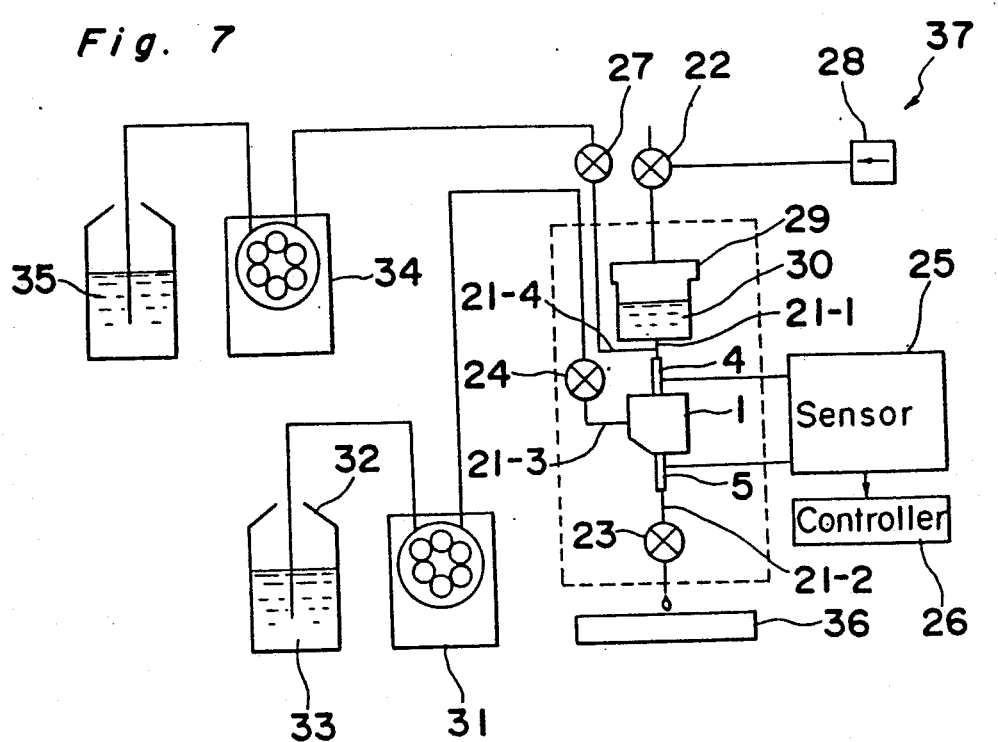
FIG. 7 is a diagram similar to FIG. 2, showing a modified form of a particle analyzing system.

The particle analyzer according to this embodiment is generally identified by 13D in FIGS. 6(a) to 6(c). The particle analyzer 13A comprises a solid block having defined therein a generally elongated constricted passage 1 for the passage of fine particles in suspension therethrough for separation, said constricted passage 1 having its opposite end communicated respectively with upstream and downstream passages 2 and 3; a cleansing passage 7 having one end communicated to a source of cleansing liquid and the other communicated with the downstream passage 3 adjacent the constricted passage 2; and a diluting liquid passage 17.

Where the particle analyzer 13D of the construction shown in FIG. 6 is used in a particle analyzing system, the particle analyzing system is so designed and so assembled as shown in FIG. 7.

Referring now to FIG. 7, the particle analyzing system shown therein is substantially identical with that shown in and described with reference to FIG. 2 except that a diluting liquid supply passage 21-4 having an electromagnetic valve 27 disposed thereon is communicated with a diluting liquid tank 35 through a rotary pump 34 as shown.

In operation, when the particles in the suspension are desired to be detected with the particle analyzing system 37, the electromagnetic valve 22 is opened and, on the other hand, the pump 28 is operated to apply a gas pressure to the suspension 30 within the tank 29. The application of the gas pressure thus causes the suspension 30 to flow towards the particle analyzer 13A through the supply piping 21-1 and then towards the collecting vessel 36 through the discharge piping 21-2 after having passed through the constricted passage 1 in the particle analyzer 13A. At this time, the electromagnetic valves 23 and 24 are closed.

As the particles contained in the suspension pass through the constricted passage 1, the sensor 25 detects the change in impedance, thereby to detect the number of the particles per volume of the suspension in reference to time and the flow of the suspension.

Where the number of the particles per volume detected is great, the electromagnetic valve 27 is opened to allow the diluting liquid within the vessel 35 to be pumped by the rotary pump 34 so as to flow into the upstream passage 2 through the diluting liquid passage 8 and then through the constricted passage 1. Consequent upon this, the suspension then flowing through the constricted passage 1 can be diluted so as to adjust the density of the particles in the suspension to a proper value.

When the sensor 25 detects the change in impedance induced by the flow of the diluted suspension through the constricted passage 1 and subsequently generates a detection output signal which is in turn applied to the controller 26. In response to the output signal from the sensor 25, the controller 26 issues disabling commands to the electromagnetic valves 22, 23 and 24, respectively, thereby to interrupt the supply of the diluted suspension.

However, when the electromagnetic valves 22 and 23 are opened while the electromagnetic valves 22, 23 and 24 remain closed, the rotary pump 31 is operated to cause the cleansing liquid 33 to be supplied from the liquid vessel 32 towards the particle analyzer 13A through the electromagnetic valve 24 by way of the liquid piping 21-3 and, then, through the cleansing passage 7 into the downstream passage 3 while purging into the collecting vessel 36 the fine particles which have passed through the constricted passage 1. Where the fine particles are desired to be individually collected each in one vessel, a row of vessels 36 should be conveyed to a position immediately below the discharge piping 21-2 and, for this purpose, a conveyor carrying the vessels 36 may be controlled in dependence on the output signal generated from the sensor 25.

Figure 8:
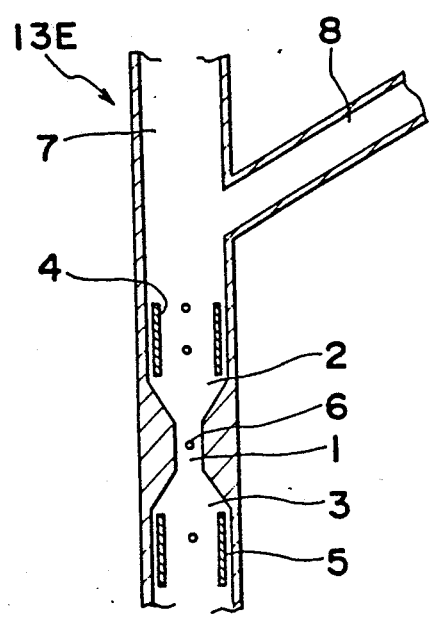
FIG. 8 is a longitudinal sectional view of a further modified form of the particle analyzer.
Figure 10:
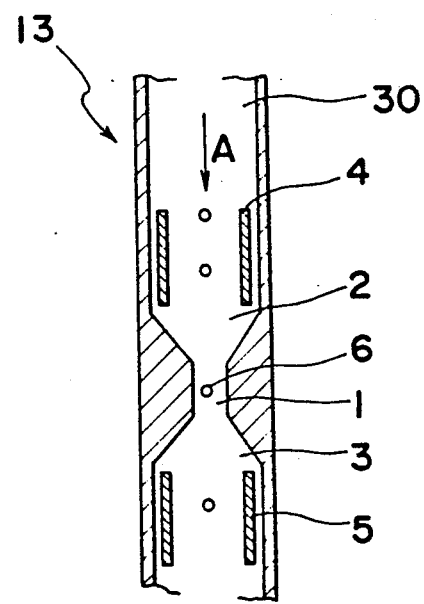
FIG. 10 is a longitudinal sectional view of the prior art particle analyzer.

In the embodiment shown in FIGS. 6 and 7, the use is made of the cleansing passage 7 communicated with the downstream passage 3 immediately below the constricted passage 1 so that the fine particles having passed through the constricted passage 1 can be flushed out by the cleansing liquid supplied through the cleansing passage 7, thereby to accomplish the separation of the individual fine particles accurately. Where the accuracy of the separation of the individual fine particles is not required so much, such a particle analyzer as shown by 13E in FIG. 8 may be employed wherein the constricted passage 1 is formed in a duct for the flow of the suspension therethrough and the upstream and downstream electrodes 4 and 5 are disposed on upstream and downstream sides of the constricted passage 1 with the cleansing passage 7 communicated with the upstream side.

Figure 9:
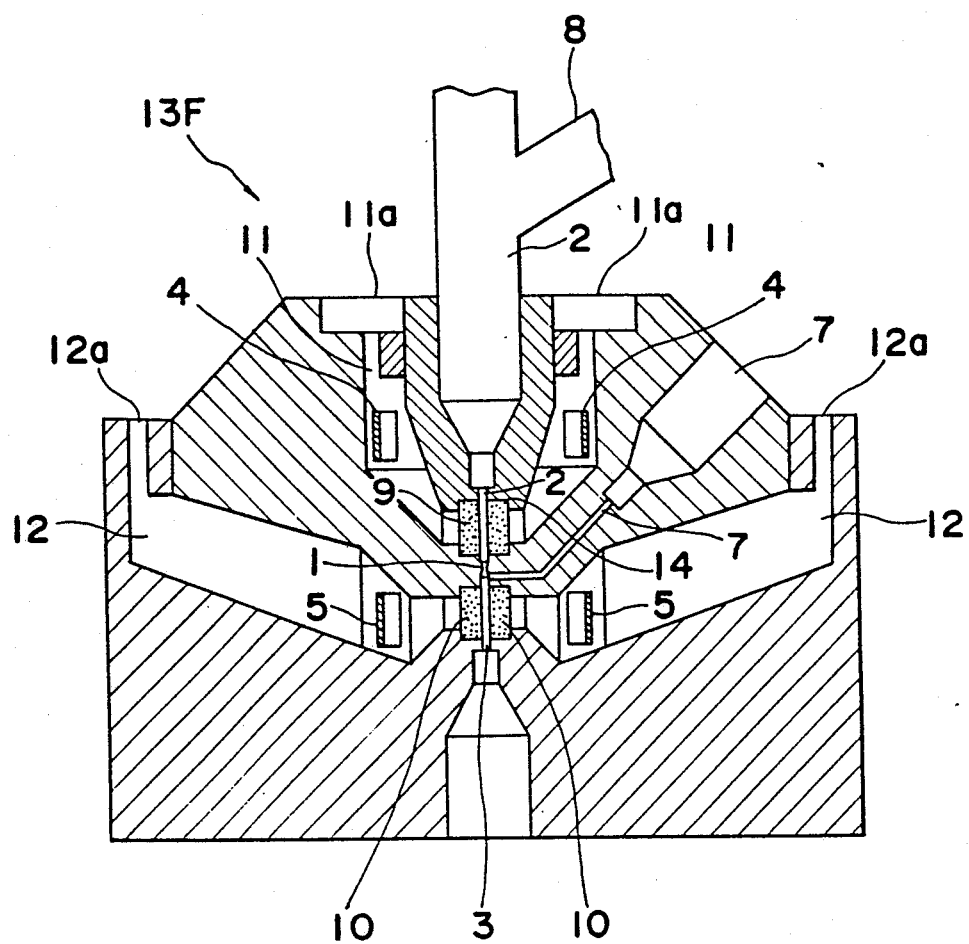
FIG. 9 is a longitudinal sectional view of the particle analyzer according to a still further embodiment of the present invention.

(Embodiment V)

Where the particle analyzer of the construction shown in and described with reference to FIG. 6 is used and where there is a possibility that bubbles of hydrogen gas produced as a result of hydrolysis of water which takes place when an electric current is supplied across the upstream and downstream electrodes 4 and 5 may be erroneously taken as the fine particles to be detected, the particle analyzer of a construction shown in FIG. 9 may be employed. The particle analyzer identified by 13F in FIG. 9 is substantially identical in construction and operation with that shown in and described with reference to FIG. 5 except that the diluting liquid passage 8 is communicated with the upstream passage 2 as shown in FIG. 9.

Although the present invention has fully been described in connection with the preferred embodiments thereof with reference to the accompanying drawings, it is to be noted that various changes and modifications are apparent to those skilled in the art. Such changes and modifications are to be understood as included within the scope of the present invention unless they depart therefrom.

What is claimed is:

1. A particle analyzer which comprises:
structure defining a constricted passage through which fine particles contained in a suspension may pass;
structure defining upstream and downstream passages, the upstream and downstream passages each being communicated with the constricted passage and positioned respectively on upstream and downstream sides of the constricted passage with respect to the direction of flow of the suspension;
a detecting means including upstream and downstream electrodes disposed in their respective upstream and downstream passages, respectively, for detecting the fine particles being passed through the constricted passage, the upstream electrode being positioned on respective sides of the constricted passage with a first porous member intervening between the upstream electrodes and the constricted passage, the downstream electrodes being positioned on respective sides of the constricted passage with a second porous member intervening between the downstream electrodes and the constricted passage, each of the first and second porous members having micropores effective to allow ions to pass and to block particles of a size comparable to the fine particles; and
structure defining a cleansing passage communicated with either the upstream or downstream passage for the supply of a cleansing liquid.

2. A particle analyzing system which comprises:
a particle analyzer comprising structure defining a constricted passage through which fine particles contained in a suspension may pass, upstream and downstream passages, the upstream and downstream passages each being communicated with the constricted passage and positioned respectively on upstream and downstream sides of the constricted passage with respect to the direction of flow of the suspension, a detecting means including upstream and downstream electrodes disposed in their respective upstream and downstream passage means for detecting the fine particles being passed through the constricted passage said upstream electrodes being positioned on respective sides of the constricted passage with a first porous member intervening between the upstream electrodes and the constricted passage, the downstream electrode being positioned on respective sides of the constricted passage with a second porous member intervening between the downstream electrodes and the constricted passage, each of the first and second porous members having micropores effective to allow ions to pass and to block particles of a size comparable to the fine particles, and a cleansing passage communicated with either the upstream or downstream passages for the supply of a cleansing liquid;
a container for accommodating the suspension and communicated with the upstream passage, the suspension being supplied to the particle analyzer by means of a valving operation;
a discharge piping leading from the downstream passage to a discharge port and having a valve disposed thereon for controlling the discharge of the suspension which has flowed through the constricted passage;
a cleansing liquid supply piping extending from a source of the cleansing liquid to the cleansing passage and having a valve disposed thereon for controlling the supply of the cleansing liquid; and
a sensor included in the detecting means for detecting the change in impedance between the upstream and downstream electrodes.

3. A particle analyzer which comprises:
a constricted passage for the passage of fine particles contained in a suspension therethrough for isolation;
upstream and downstream passage communicated with the constricted passage and positioned on upstream and downstream sides of the constricted passage with respect to the direction of flow of the suspension;
a diluting liquid passage communicated with the upstream passage for the supply of a diluting liquid;
a detecting means including upstream and downstream electrodes disposed in the upstream and downstream passage, respectively, so as to confront with each other for detecting the fine particles being passed through the constricted passage; and
a cleansing passage communicated with either one of the upstream and downstream passage for the supply of a cleansing liquid.

4. A particle analyzing system which comprises:
a particle analyzer comprising a constricted passage for the passage of fine particles contained in a suspension therethrough for isolation, upstream and downstream passage communicated with the constricted passage and positioned on upstream and downstream sides of the constricted passage with respect to the direction of flow of the suspension, a diluting liquid passage communicated with the upstream passage for the supply of a diluting liquid, a detecting means including upstream and downstream electrodes disposed in the upstream and downstream passage, respectively, so as to confront with each other for detecting the fine particles being passed through the constricted passage, and a cleansing passage communicated with either one of the upstream and downstream passage for the supply of a cleansing liquid;

a container for accommodating the suspension and communicated with the upstream passage, said suspension being supplied to the particle analyzer by means of a valving operation;

a discharge piping leading from the downstream passage to a discharge port and having a valve disposed thereon for controlling the discharge of the suspension which has flowed through the constricted passage;

a diluting liquid supply piping extending from a source of diluting liquid to the upstream passage and having a valve disposed thereon for controlling the flow of the diluting liquid from the source of diluting liquid to the upstream passage;

a cleansing liquid supply piping extending from a source of the cleansing liquid to the cleansing passage and having a valve disposed thereon for controlling the supply of the cleansing liquid; and a sensor included in the detecting means for detecting the change in impedance between the upstream and downstream electrodes.

5. A particle analyzer which comprises:

structure defining a constricted passage through which fine particles contained in a suspension may pass;

structure defining upstream and downstream passages, the upstream and downstream passages each being communicated with the constricted passage and positioned respectively on upstream and downstream sides of the constricted passage with respect to the direction of flow of the suspension;

a detecting means including upstream and downstream electrodes disposed in their relative upstream and downstream passages, for detecting the fine particles being passed through the constricted passage, the upstream electrodes being positioned on respective sides of the constricted passage with a first porous member intervening between the upstream electrodes and the constricted passage, the downstream electrodes being positioned on respective sides of the constricted passage means with a second porous member intervening between the downstream electrodes and the constricted passage, each of said first and second porous members having micropores which allow ions to pass, and block particles of a size comparable to the fine particles;

structure defining a diluting liquid passage communicated with the upstream passage the diluting liquid passage supplying a diluting liquid therethrough; and structure defining a cleansing passage communicated with either the upstream or downstream passages, the cleaning passage supplying a cleansing liquid.

6. A particle analyzing system which comprises:

a particle analyzer comprising structure defining a constricted passage through which fine particles contained in a suspension may pass, upstream and downstream passages, the upstream and downstream passages each being communicated with the constricted passage and positioned respectively on upstream and downstream sides of the constricted passage with respect to the direction of flow of the suspension, a detecting means including upstream and downstream electrodes disposed in their respective upstream and downstream passages for detecting the fine particles being passed through the constricted passage, the upstream electrodes being positioned on respective sides of the constricted passage with a first porous member intervening between the upstream electrodes and the constricted passage, the downstream electrodes being positioned on respective sides of the constricted passage with a second porous member intervening between the downstream electrodes and the constricted passage, each of the first and second porous members having micropores which allow ions to pass and which block particles of a size comparable to the fine particles, structure defining a diluting liquid passage communicated with the upstream passage, the diluting liquid passage supplying a diluting liquid; and structure defining a cleansing passage communicated with either of the upstream or downstream passages, the cleansing passage supplying a cleansing liquid;

a container for accommodating the suspension and communicated with the upstream passage; said suspension being supplied to the particle analyzer by means of a valving operation;

a discharge piping leading from the downstream passage to a discharge port and having a valve disposed thereon for controlling the discharge of the suspension which has flowed through the constricted passage;

a diluting liquid supply piping extending from a source of diluting liquid to the upstream passage and having a valve disposed thereon for controlling the flow of the diluting liquid towards the diluting liquid passage;

a cleansing liquid supply piping extending from a source of the cleansing liquid to the cleansing passage and having a valve disposed thereon for controlling the supply of the cleansing liquid; and a sensor included in the detecting means for detecting the charge in impedance between the upstream and downstream electrodes.

* * * * *